United States Patent [19]

King

[11] Patent Number: 4,697,019

[45] Date of Patent: Sep. 29, 1987

[54] AZABICYCLO COMPOUNDS, USEFUL AS INTERMEDIATES

[75] Inventor: Francis D. King, Newport, England

[73] Assignee: Beecham Group p.l.c., Epsom, England

[21] Appl. No.: 824,205

[22] Filed: Mar. 21, 1986

Related U.S. Application Data

[62] Division of Ser. No. 484,317, Apr. 12, 1983, Pat. No. 4,612,319.

[30] Foreign Application Priority Data

Apr. 14, 1982 [GB] United Kingdom ............... 8210847
Apr. 14, 1982 [GB] United Kingdom ............... 8210848

[51] Int. Cl.$^4$ ................ C07D 221/04; C07D 223/14
[52] U.S. Cl. ................................. 546/112; 540/582; 540/477
[58] Field of Search ............... 546/112; 540/477, 582

[56] References Cited

U.S. PATENT DOCUMENTS 4,182,884  1/1980  Wong ................................. 546/112
4,336,259  6/1982  Hadley et al. ..................... 546/112

FOREIGN PATENT DOCUMENTS 0013138  7/1980  European Pat. Off. ............ 546/112
0036269  9/1981  European Pat. Off. ............ 546/112
2748260  5/1978  Fed. Rep. of Germany ...... 546/112

OTHER PUBLICATIONS

Chizhov et al., Chem. Abstracts, vol. 53, p. 21958e, (1959).
O. Oldenziel, D. van Leusen, and A. van Leusen, "A General One-Step Synthesis of Nitriles from Ketones Using Tosylmethyl Isocyanide, Introduction of a One Carbon Unit," *J. Org. Chem.*, 42, pp. 3114–3118, (1977).
P. Protais, J. Costentin and J. C. Schwartz, "Climbing Behavior Induced by Apomorphine in Mice, A Simple Test for the Study of Dopamine Receptors in Striatum," *Psychopharmacology*, 50, pp. 1–6, (1976).

Primary Examiner—John M. Ford
Assistant Examiner—J. Richter
Attorney, Agent, or Firm—James F. Haley, Jr.; James W. Brady, Jr.

[57] ABSTRACT

A compound of formula (XXII):

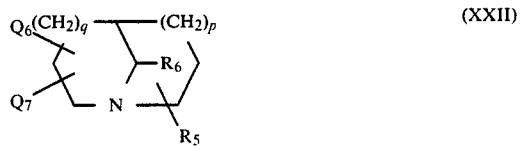

or a compound of formula (XXIII):

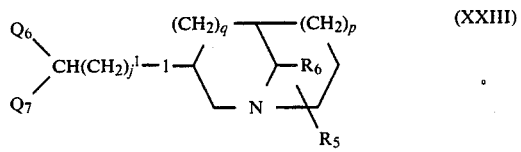

wherein in formula (XXIII), $j^1-1$ is 1 to 4; and $Q_6$ and $Q_7$ are on the same carbon atom; and wherein, in formulae (XXII) and (XXIII), $Q_6$ is $NH_2$ and $Q_7$ is H, and either p is 0 to 2 and q is 1; or p is 1 and q is 0 to 3; and one of $R_5$ and $R_6$ is hydrogen, $C_{1-6}$ alkyl, phenyl or phenyl —$C_{1-3}$ alkyl, which phenyl moieties may be substituted by $C_{1-6}$ alkyl, $C_{1-6}$ alkoxy, $CF_3$ or halogen; and the other of $R_5$ and $R_6$ is hydrogen or $C_{1-6}$ alkyl.

11 Claims, No Drawings

AZABICYCLO COMPOUNDS, USEFUL AS INTERMEDIATES

This application is a division of co-pending U.S. patent application Ser. No. 484,317, filed Apr. 12, 1983, now U.S. Pat. No. 4,612,319.

This invention relates to pharmacologically active compounds, to a process for their preparation, and to a pharmaceutical composition containing them.

West German Offenlegungsschrift No. 27 48 260.6 discloses that compounds of the formula (A), and their pharmaceutically acceptable salts:

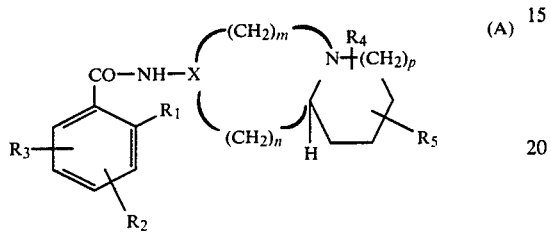

wherein
$R_1$ is a $C_{1-6}$ alkoxy group;
$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acyl amino, aminocarbonyl or aminosulphone optionally substituted by one or two $C_{1-6}$ alkyl groups, $C_{1-6}$ alkylsulphone or nitro groups;
X is either a nitrogen atom, in which case m+n is 3 to 5, m is 2 to 4 and n is 1 to 3; or X is CH in which case m+n is 2 to 5; m is 1 to 5, and n is 0 to 4;
p is 0 to 3;
$R_4$ is hydrogen, $C_{1-6}$ alkyl, phenyl or phenyl $C_{1-6}$ alkyl, either of which phenyl moiety may be substituted by $C_{1-6}$ alkyl, $C_{1-6}$ alkoxy, $CF_3$ or halogen, and $R_5$ is hydrogen; or $R_4$ and $R_5$ are attached to two adjacent carbon atoms and form together with these two carbon atoms a fused benzene ring, which benzene ring may be substituted by $C_{1-6}$ alkyl, $C_{1-6}$ alkoxy, $CF_3$ or halogen; have useful pharmaceutical activity. For example, it was disclosed that such compounds may be used for treatment of disorders of the gastro-intestinal function, such as retarded gastric emptying, dyspepsia, flatulence, oesophageal, reflux, peptic ulcer and the like; and/or for the treatment of emesis.

It has now been discovered that a class of compounds structurally distinct from those compounds of the formula (A) also have useful pharmacological activity, in particular, dopamine antagonist activity.

Accordingly the present invention provides a compound of formula (I), or a pharmaceutically acceptable salt, or N-oxide thereof, or a solvate of any of the foregoing:

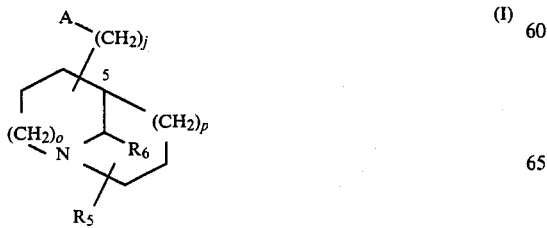

The numbering in the formulae herein is used for convenient reference in the description hereinafer, and does not necessarily correspond to IUPAC nomenclature.

In formula (I):
p is 0 to 2; q is 0 to 3; j is 0 to 4;
one of $R_5$ and $R_6$ is hydrogen, $C_{1-6}$ alkyl, phenyl or phenyl-$C_{1-3}$ alkyl, which phenyl moieties may be substituted by $C_{1-6}$ alkyl, $C_{1-6}$ alkoxy, $CF_3$ or halogen; and the other of $R_5$ and $R_6$ is hydrogen or $C_{1-6}$ alkyl; and A is of formula (II):

wherein $R_2$, $R_3$ and $R_4$ are each independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ carboxylic acylamino, $C_{1-6}$ alkylsulphonylamino, N-($C_{1-6}$ alkylsulphonyl)-N-$C_{1-4}$ alkylamino, $C_{1-6}$ alkylsulphonyl, $C_{1-6}$ alkylsulphinyl, hydroxy, nitro or amino, aminocarbonyl, aminosulphonyl, aminosulphonylamino or N-(aminosulphonyl)-N-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene; or any two together are $C_{1-2}$ alkylenedioxy;

(i) $R_1$ is independently any one of the values for $R_2$, $R_3$ or $R_4$ except hydrogen, or together with $R_2$ is $C_{1-2}$ alkylenedioxy, $C_{1-2}$ oxyalkylenethio, $C_{2-3}$ alkyleneoxy or N-($C_{1-2}$ oxyalkylene)-N-$C_{1-6}$ alkylamino; and one of X and Y is CO and the other is NH; or (ii) X is CO and Y is $NR_{16}$ where $R_1$ and $R_{16}$ together are $C_{1-2}$ alkylene; or (ii) A is of formula (III):

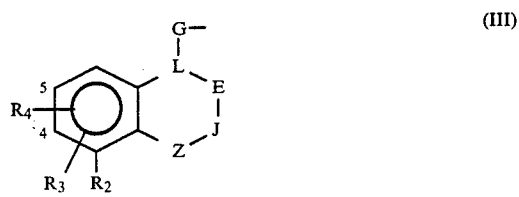

wherein:
$R_2$, $R_3$ and $R_4$ are as defined in formula (II); G is $-N=$ or $-NR_{13}$ where $R_{13}$ is hydrogen or $C_{1-4}$ alkyl;
L is $>C<$;
E, J and Z are each independently $-CHR_{14}$, $-CR_{14}=$, $-N=$ or $-NR_{15}$ where $R_{14}$ is hydrogen, $C_{1-4}$ alkyl or $C_{1-4}$ alkylthio, and $R_{15}$ is hydrogen or $C_{1-4}$ alkyl, or one of E, J and Z is C: $Z_2$ where $Z_2$ is O or S and the other two are each independently $-CR_{14}=$, $-N=$ or $-NR_{15}$ where $R_{14}$ and $R_{15}$ are as defined; or E is a bond, one of J and Z is $-CHR_{14}=$, $-N=$ or $-NH_{15}$ as defined and the other is $-CHR_{14}=$, $-N=$, O or S; or (iv) A is of formula (IV):

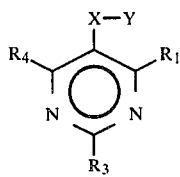

(IV)

wherein
one of X and Y is CO and the other is NH:
$R_1$, $R_3$ and $R_4$ are as defined in formula (II), except that none is combined with any other variable to form a divalent group; and
the nitrogen atom depicted in formula (I) is separated from the nearest nitrogen atom in the moiety A by at least 2 carbon atoms.

Suitable examples of $R_5$ and $R_6$ include hydrogen, methyl, ethyl, n- and iso-propyl, n-, sec- and tert-butyl; phenyl, phenylmethyl and phenylethyl, which phenyl moieties may be substituted by one or two methyl, ethyl, n- and iso-propyl, n-, sec- and tert-butyl; methoxy, ethoxy and n- and iso-propoxy; $CF_3$, fluoro, chloro or bromo.

Suitably j may be 0, 1 or 2; preferably j is 1; j is also preferably 0.

Suitably p may be 0, 1 or 2, preferably 1.

Suitably q may be 0, 1 or 2, more suitably 1 or 2, preferably 1.

Often p and q will both be 1 or 2, preferably they will both be 1.

Examples of $C_{1-4}$ or $C_{1-6}$ alkyl groups for or within all variables hereinafter include methyl, ethyl, n- and iso-propyl and n-, sec- and tert-butyl, preferably methyl.

Suitably one of $R_2$, $R_3$ and $R_4$ is hydrogen and the other two are together methylenedioxy or ethylenedioxy or are each independently hydrogen, chloro, bromo, $CF_3$, methyl, methoxy, ethoxy, n- or iso-propoxy, methylthio, ethylthio, n- or iso-propylthio, formylamino, $C_{1-4}$ alkanoylamino such as acetylamino, propionylamino, n- or iso-butyrylamino, nitro or amino or aminosulphonyl optionally N-substituted by one or two methyl, cyclopropylmethyl, cyclopentyl groups or tetramethyl.

Preferably the other two of $R_2$, $R_3$ and $R_4$ are independently hydrogen, chloro, bromo, methoxy, amino, aminosulphonyl, optionally substituted as defined, $C_{1-6}$ alkylsulphonyl, $C_{1-6}$ alkylsulphinyl, $CF_3$ or methyl.

When A is of formula (II) and $R_2$ is independently one of the values of $R_2$, $R_3$ or $R_4$, suitable values for $R_1$ are as for $R_2$, $R_3$ and $R_4$ above. Preferred values for $R_1$ are as for $R_2$, $R_3$ and $R_4$ above, in particular methoxy.

Alternatively, $R_1$ and $R_2$ together are $C_{1-2}$ alkylenedioxy, and suitable and preferred $R_3$ and $R_4$ values are then as for $R_3$ and $R_4$ above.

In the foregoing cases, $R_2$ is preferably hydrogen, $R_3$ is preferably in the 4-position as defined in formula (II) and $R_4$ is preferably in the 5-position as defined in formula (II).

Particularly preferred values of $R_3$ include hydrogen, methoxy, amino and methyl, especially in the 4-position as defined. Particularly preferred values of $R_4$ include hydrogen, chloro, bromo, methoxy, aminosulphonyl optionally substituted as defined, $C_{1-6}$ alkylsulphonyl, $C_{1-6}$ alkylsulphinyl or $CF_3$, especially in the 5-position as defined.

When A is of formula (III) as defined, suitable values of the moiety GLEJZ include:

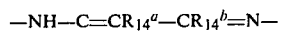

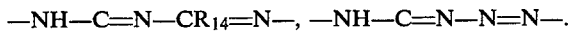

Suitable values also include $—N=C—NR_{15}{}^a—C-B—NR_{15}{}^b—$, where $R_{14}{}^a$ and $R_{14}{}^b$ are the same or different $R_{14}$ values as hereinbefore described, and $R_{15}{}^a$ and $R_{15}{}^b$ are the same or different $R_{15}$ values as hereinbefore described.

Preferred values include $—NH—C=N—CR_{14}=N—$, in particular $—NH—C=N—CH=N—$.

In the above cases, it is generally preferred that $R_2$ is hydrogen, $R_3$ is in the 4-position as defined in formula (III), and $R_4$ is in the 5-position as defined in formula (III).

Particularly preferred values of $R_3$ include hydrogen, halo such as chloro or bromo, and amino, especially in the 4-position as defined. Particularly preferred values of $R_4$ include hydrogen, halo such as chloro or bromo, optionally substituted aminosulphonyl as defined such as dimethylaminosulphonyl, $C_{1-6}$ alkysulphonyl, $C_{1-6}$ alkylsulphinyl and $C_{1-6}$ alkylthio, especially in the 5-position as defined.

When A is of formula (IV), suitably $R_1$, $R_3$ and $R_4$ are as so described for corresponding $R_1$, $R_3$ and $R_4$ when A is of formula (II), that is $R_1$, $R_3$ and $R_4$ not combined with any other variable.

Preferred $R_1$ and particularly preferred $R_3$ are as so described for $R_1$ and $R_3$ when A is of formula (II).

$R_4$ is preferably hydrogen.

Preferably the nitrogen atom depicted in formula (I) is separated from the nearest nitrogen atom in the moiety A by at least 2 carbon atoms.

The pharmaceutically acceptable salts of the compounds of formula (I) include acid addition salts with inorganic acids such as hydrochloric, hydrobromic, boric, phosphoric, sulphuric and pharmaceutically acceptable organic acids such as acetic, tartaric, maleic, citric, succinic, benzoic, ascorbic, methanesulphonic, α-ketoglutaric, α-glycerophosphoric, and glucose-1-phosphoric; and quaternary ammonium salts. Preferably the acid addition salt is a hemisuccinate, hydrochloride, α-ketoglutarate, α-glycerophosphate or glucose-1-phosphate, in particular the hydrochloride salt.

Examples of quaternary ammonium salts include such compounds quaternised by compounds such as $R_8$-Q wherein $R_8$ is $C_{1-6}$ alkyl, phenyl-$C_{1-6}$ alkyl or $C_{5-7}$ cycloalkyl, and Q is a radical corresponding to a anion of an acid. Suitable examples of $R_8$ include methyl, ethyl and n- and iso-propyl; and benzyl and phenethyl. Suitable examples of Q include halides such as chloride, bromide and iodide.

The pharmaceutically acceptable salts of the compounds of the formula (I) are usually acid addition salts with conventional acids such as hydrochloric, hydrobromic, phosphoric, sulphuric, citric, tartaric, lactic and acetic acid.

The compounds of formula (I) may also form pharmaceutically acceptable N-oxides.

The compounds of the formula (I) and their pharmaceutically acceptable salts and N-oxides may also form solvates.

It will of course be realised that the compounds of the formula (I) have at least one chiral centre, viz. that numbered 5 in formula (I). The compounds may also have other chiral or prochiral centres and, in formula (III) when —G—L= is —N=C—, a non-symmetrical centre, and thus are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

From the aforesaid, it will be seen that suitably the moiety A may be of formulae:

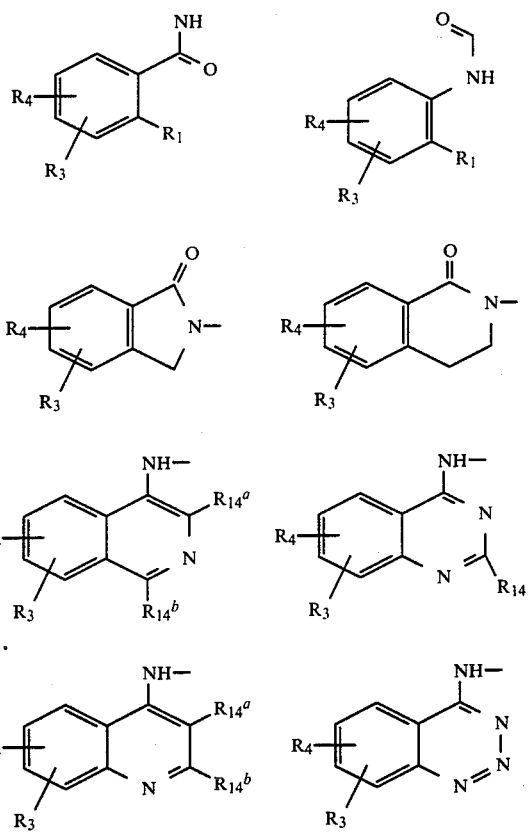

in particular, of formulae:

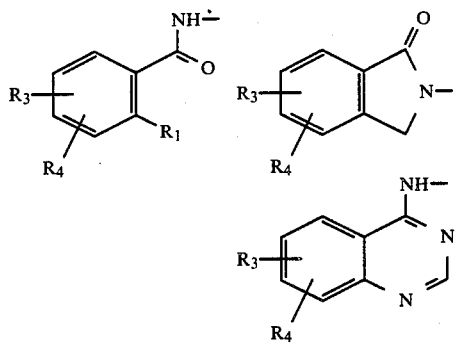

A group of compounds within formula (I) is of formula (V):

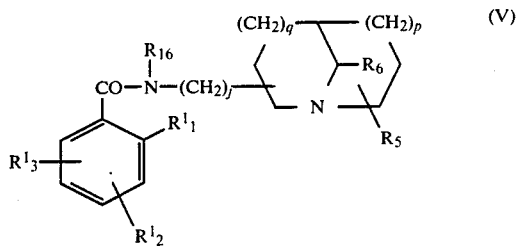

wherein:
$R^1{}_1$ is a $C_{1-6}$ alkoxy group;
$R^1{}_2$ and $R^1{}_3$ are the same or different and are hydrogen, halogen, $CF_3$, $C_{1-7}$ acyl, $C_{1-7}$ carboxylic acylamino, $C_{1-6}$ alkyl-$S(O)_n$ wherein n is 0, 1 or 2, nitro, or amino, aminocarbonyl or aminosulphonyl optionally substituted by one or two $C_{1-6}$ alkyl groups;
or $R^1{}_1$ and $R^1{}_2$ taken together are methylenedioxy or ethylenedioxy in which case $R^1{}_3$ is any one of the groups given for $R^1{}_1$ and $R^1{}_2$ above;
$R_{16}$ is hydrogen or $C_{1-6}$ alkyl;
one of $R_5$ and $R_6$ is hydrogen, $C_{1-6}$ akyl, phenyl or phenyl-$C_{1-3}$ alkyl, which phenyl moieties may be substituted by $C_{1-6}$ alkyl, $C_{1-6}$ alkoxy, $CF_3$ or halogen;
and the other of $R_5$ and $R_6$ is hydrogen or $C_{1-6}$ alkyl;
j is 0 to 4;
p is 0 to 2;
q is 0 to 3; and
the two nitrogen atoms in the amide side chain are spaced by at least two carbon atoms.

Another group of compounds wthin formula (I) is of formula (VI):

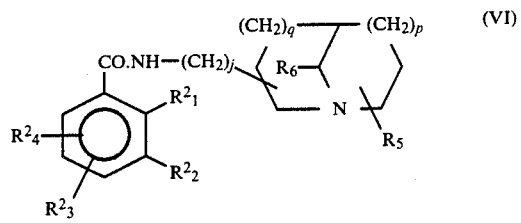

wherein:
$R^2{}_1$ is $C_{1-6}$ alkoxy or amino N-substituted by one or two groups selected from $C_{1-6}$ alkyl or $C_{3-8}$ cycloalkyl or optionally N-substituted by $C_{4-5}$ polymethylene;
one of $R^2{}_2$, $R^2{}_3$ and $R^2{}_4$ is hydrogen and the other two are independently selected from hydrogen, chloro, bromo, trifluoromethyl, hydroxy, $C_{1-6}$ alkoxy, $C_{1-6}$ alkylthio, $C_{1-6}$ alkyl, amino, $C_{1-6}$ alkylsulphonyl, $C_{1-6}$ alkylsulphinyl or aminosulphonyl optionally N-substituted by one or two $C_{1-6}$ alkyl group or $C_{4-5}$ polymethylene; or
$R^2{}_1$ and $R^2{}_2$ together are methylenedioxy or ethylenedioxy and $R^2{}_3$ and $R^2{}_4$ are the same or different and are selected from the previously defined class of substituents and the remaining variables are as defined in formula (I).

Suitable and preferred variables are as so described for corresponding variables in relation to formula (I).

A second sub-group of compounds within formula (VI) is of formula (VII):

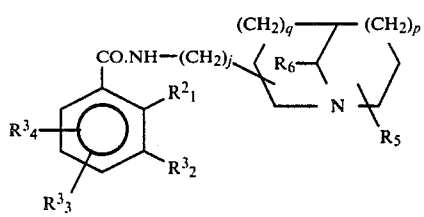

(VII)

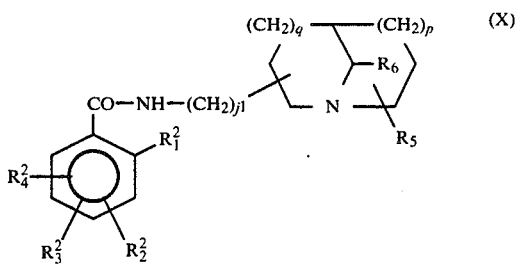

(X)

wherein one of $R^3_2$, $R^3_3$ and $R^3_4$ is hydrogen, and the other two are independently selected from hydrogen, chloro, bromo, trifluoromethyl, hydroxy, $C_{1-6}$ alkoxy, $C_{1-6}$ alkylthio, $C_{1-6}$ alkyl and amino; and the remaining variables are as defined in formula (VI).

Suitable and preferred variables are as so described for corresponding variables in relation to formula (I).

A second sub-group of compounds within formula (VI) is of formula (VIII):

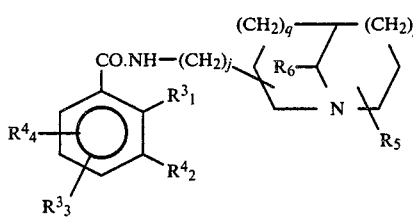

(VIII)

wherein
$R^4_4$ is $C_{1-6}$ alkylsulphonyl, $C_{1-6}$ alkylsulphinyl, or aminosulphonyl optionally N-substituted by one or two $C_{1-6}$ alkyl groups or $C_{4-5}$ polymethylene; and
$R^3_1$ is $R^2_1$ as defined and $R^4_2$ is hydrogen; or
$R^3_1$ and $R^4_2$ together are $C_{2-3}$ alkylenedioxy or $C_{2-3}$ alkyleneoxy;
and the remaining variables are as defined in formula (I).

Suitable and preferred variables are as so described for corresponding variables in relation to formula (I).

A third sub-group of compounds within those of formula (VI) is of formula (IX):

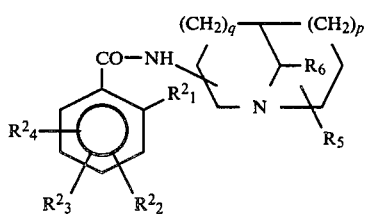

(IX)

wherein the variables are as defined in formula (VI).

Suitable and preferred variable values in formula (IX) are as so described under formula (VI).

A fourth sub-group of compounds within those of formula (VI) is of formula (X):

wherein $j^1$ is 1 to 4 and the remaining variables are as defined in formula (VI).

$j^1$ may suitably be 1 or 2, preferably 1.

Suitable and preferred other variables are as so described under formula (VI).

From the aforesaid, it will be seen that suitably the moiety of formula (XI):

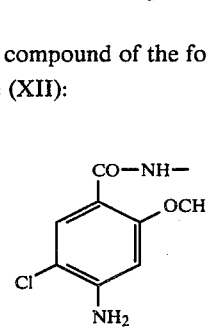

(XI)

in a compound of the formula (VI) will have the structure (XII):

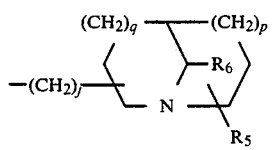

(XII)

Similarly in a preferred group of compounds within those of formula (VI), the moiety of formula (XIII):

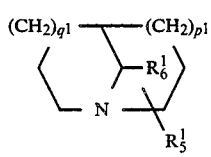

(XIII)

is of formula (XIV):

(XIV)

or of formula (XV):

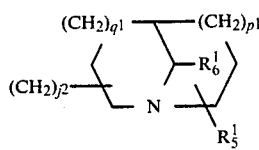 (XV)

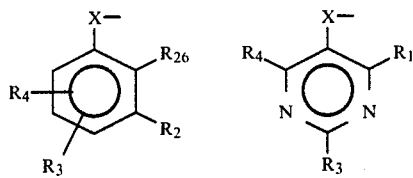

wherein:
$R^1_5$ is hydrogen or $C_{1-6}$ alkyl;
$R^1_6$ is hydrogen or $C_{1-6}$ alkyl;
$j^2$ is 1 or 2;
$p^1$ is 0, 1 or 2; and
$q^1$ is 1 or 2.

In formula (XV) preferably $R^1_5$ and $R^1_6$ are separately hydrogen or methyl. In one such arrangement, $R^1_5$ is hydrogen and $R^1_6$ is methyl.

Preferably $p^1$ and $q^1$ are both 1.
Preferably $j^2$ is 1.

When $j^2$ is 1, most suitably in formula (XV) the —$(CH_2)_{j^2}$— group joins the ring at a carbon atom B to the ring nitrogen.

A preferred group of compounds within formula (VI) is therefore of formula (XVI):

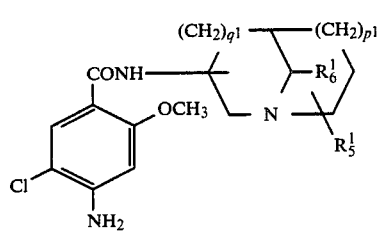 (XVI)

wherein the variables are as defined in formula (XIV).

Suitable and preferred variables are as so described under formulae (XIV) and (XV).

One compound of the invention that is particularly preferred for its useful activity is Example 9 hereinafter.

A second preferred group of compounds within formula (VI) is therefore of formula (XVII):

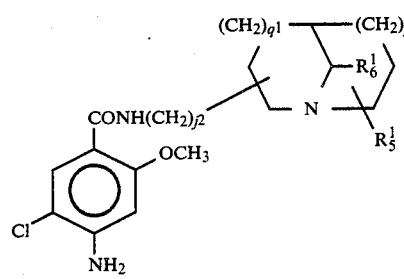 (XVII)

wherein the variables are as defined in formula (XV).

Suitable and preferred variables are as so described under formulae (XIV) and (XV).

The invention also provides a process for the preparation of a compound of the formula (I), which process comprises reacting a compound of the formula (XVIII):

$$TQ_1 \quad (XVIII)$$

wherein T is of the formula (XIX) or (XX):

wherein $R_2$, $R_3$ and $R_4$ are as defined in formula (II) or (IV) respectively; and (i) X is CO and $Q_1$ is a group readily displaceable by a nucleophile or X is NH and $Q_1$ is H; and $R_{26}$ and $R_1$ are monovalent $R_1$ as defined in formula (II) or (IV); $R_{26}$ together with $R_2$ forms a divalent group as defined in formula (II); or (ii) X is CO and $Q_1$ is a group readily displaceable by a nucleophile; and $R_{26}$ is a group $(CH_2)_sCR_{17}R_{18}Q_2$ where s is 0 or 1, $R_{17}$ and $R_{18}$ are each H or together are O and $Q_2$ is a group readily displaceable by a nucleophile, or together with $Q_1$ is O;

or T is of formula (XXI):

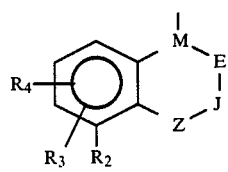 (XXI)

where
Rhd 2, $R_3$, $R_4$, E, J and Z are as defined in formula (III);
M is >C< and $Q_1$ is a group readily displaceable by a nucleophile, $NH_2$, or, when one of E, J and Z is —N= and the others are —$CR_{14}$= or —N= as defined, hydrogen; or M is =$CQ_5$— where $Q_5$ is halo and $Q_1$ is halo or $Q_1$ and $Q_5$ together are oxo or thioxo;

with a compound of formula (XXII):

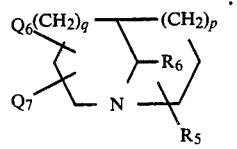 (XXII)

or with a compound of formula (XXIII):

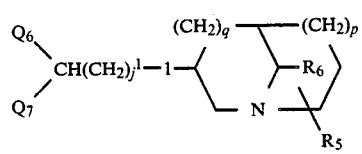 (XXIII)

wherein
in formula (XXIII),
$j^1 - 1$ is 1 to 4;
$j^1 - 1$ may suitably be 1 or 2, preferably 1.
$Q_6$ and $Q_7$ are on the same carbon atoms; and
in formulae (XXII) and (XXIII) p, q, $R_5$ and $R_6$ are as defined in formula (I); or (i) when $Q_1$ is a group readily displaceable by a nucleophile, $Q_1$ and $Q_5$ are each halo or together are oxo or thioxo, or $MQ_1$ is $=CH-$, $Q_6$ is $NH_2$ and $Q_7$ is H;

(ii) when $Q_1$ is H, $Q_6$ is $COQ_8$ where $Q_8$ is a group readily displaceable by a nucleophile, and $Q_7$ is H;

(iii) when $Q_1$ is $NH_2$, $Q_6$ and $Q_7$ together are oxo or, in formula (XXII), thioxo; or $Q_6$ is a group readily displaceable by a nucleophile, and $Q_7$ is H; and as necessary thereafter converting $R_{26}$ to $R_1$ or reducing the resulting compound to a compound of formula (I).

Examples of groups readily displaceable by a nucleophile include: for $Q_1$, $Q_2$, $Q_5$, $Q_6$ and $Q_8$, halogen such as chloro and bromo; for $Q_1$, $Q_2$ when $R_{17}$ and $R_{18}$ together are oxo and $Q_8$: hydroxy, carboxylic acyloxy such as $C_{1-4}$ alkanoyloxy, $C_{1-4}$ alkoxycarbonyloxy and, when not part of the moeity, $MQ_1$, activated hydrocarbyloxy such as pentachlorophenoxy; for $Q_1$ when part of $=MQ_1-$, $Q_2$ when $R_{17}$ and $R_{18}$ are each hydrogen and $Q_6$: labile acyloxy such as tosyloxy, mesyloxy or triflate; and for $Q_1$ when part of $=MQ_1-$: $C_{1-4}$ alkoxy such as methoxy or ethoxy, or $C_{1-4}$ alkylthio such as methylthio.

If a group $Q_1$, $Q_2$, $Q_6$ or $Q_8$ is a halide, then the reaction is preferably carried out at non-extreme temperatures in an inert non-hydroxylic solvent, such as benzene, toluene, diethyl ether, THF or DMF. It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 20°–100° C., in particular 30°–80° C. are suitable.

If a group $Q_1$, $Q_2$ or $Q_8$ is hydroxy, then the reaction is preferably carried out in an inert nonhydroxylic solvent, such as benzene, toluene or diethyl ether in the presence of a dehydrating catalyst, such as a carbodiimide, for example dicyclohexylcarbodiimide. For $Q_8$, the compound of formula (XXII) or (XXIII) is preferably in the form of an acid addition salt, such as the hydrohalide, for example the hydrochloride. The reaction may be carried out at any non-extreme temperature, such as −10° to 100° C. for example 0° to 80° C. Generally, higher reaction temperatures are employed with less active compounds whereas lower temperatures are employed with the more active compounds.

If a group $Q_1$, $Q_2$ or $Q_8$ is carboxylic acyloxy, then the reaction is preferably carried in substantially the same manner as the reaction in the presence of a dehydrating agent but without such agent. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature in the presence of an acid acceptor, such as triethylamine.

If a group $Q_1$, $Q_2$ or $Q_8$ is activated hydrocarbyloxy then the reaction is preferably carried out in an inert polar solvent, such as dimethylformamide. It is also preferred that the activated hydrocarbyloxy group is as pentachlorophenyl ester and that the reaction is carried out at ambient temperature.

If a group $Q_1$, $Q_2$ or $Q_6$ is labile acyloxy, reaction conditions are preferably as for $Q_1$, $Q_2$, $Q_6$ or $Q_8$ halide hereinbefore.

If a group $Q_1$ is alkoxy or alkylthio reaction conditions are preferably as for $Q_1$, $Q_2$, $Q_6$ or $Q_8$ halide hereinbefore.

When $Q_1$ and $Q_2$ together are O, the reaction is preferably carried out by heating a mixture of the reactants in an inert solvent to superatmospheric pressure in a pressurized container.

When $Q_1$ and $Q_5$ together or $Q_6$ and $Q_7$ together are oxo or thiooxo, the condensation is conveniently effected at non-extreme temperatures at about ambient, in a dry inert solvent, such as benzene, toluene, xylene or DMF.

When an oxo group is involved, the condensation eliminates water and it is preferable to carry out the reaction in the presence of a dehydrating agent, for example molecular sieves.

The use of a non-aqueous acid catalyst can be advantageous, for example hydrogen chloride or p-toluenesulphonic acid. Alternatively, an acid addition salt of the compound of formula (XI), (XXII) or (XXII) may be used.

When $Q_6$ and $Q_7$ together are oxo or thiooxo, the product compound must be reduced to give a compound of formula (I). This is conveniently effected in situ, and most conveniently simultaneously with the condensation.

The reduction of the product compound is conveniently simultaneously effected with a mild reducing agent, such as a mild inorganic complex hydride, for example sodium cyanoborohydride.

If a mild inorganic complex hydride reductant is used, the reaction is generally carried out in a dry, inert polar solvent, such as dry ethanol, maintained at neutral or acid pH, for example pH 5–7, with for example hydrogen chloride with pH less than 7.

Non-extreme temperatures at about ambient are generally suitable.

Alternatively, the reduction may be effected sequentially, optionally with isolation of the condensation product compound by reduction with tin/hydrochloric acid at a non-extreme temperature.

When $Q_1$ is hydrogen in $=MQ_1-$, reaction is carried out under Chichibabin conditions.

When $R_{16}$ is not $R_1$ as defined the resultant compound is not necessarily of formula (I), and $R_{16}$ must be converted to $R_1$, or the resultant compound must be reduced to one of formula (I).

When $R_{26}$ is $(CH_2)_s CR_{17}R_{18}Q_2$ as defined, coupling with elimination of both $HQ_1$ and $HQ_2$ or $H(Q_1Q_2)H$ occurs under the reaction conditions described hereinbefore. Thus where $R_{17}$ and $R_{18}$ are each H, the resulting compound is of formula (I). When $R_{17}$ and $R_{18}$ together are oxo, the resulting compound must be reduced to be of formula (I). The reduction of the group in the prepared compound is preferably carried out, with or without isolation of the compound, by hydrogenation with tin/hydrochloric acid at an elevated temperature.

It will be appreciated that it may be necessary to routinely protect $R_1$, $R_2$, $R_3$ and $R_4$ hydroxy or amino groups during the course of the reaction of compounds of the formulae (XXII) or (XXIII), to avoid unwanted side-reactions.

Suitable protected hydroxyl or amino groups include readily hydrolysable groups such as acylated hydroxy or amino groups in which the acyl moiety contains 1 to 4 carbon atoms, for example the acetoxy group; and hydroxy or amino groups alkylated by readily removable inert groups such as the benzyl group or like groups. Protected hydroxy or amino moieties may be deprotected in conventional manner. For example in a benzyloxy or benzylamino group, the benzyl group may readily be deprotected by hydrogenolysis. Thus it may be seen that 'protected hydroxy' or 'protected amino' compounds corresponding to compounds of the formula (I) are useful intermediates in the preparation of the corresponding 'free hydroxy' or 'free amino' compounds of the formula (I).

Pharmaceutically acceptable salts, and N-oxides of the compounds of this invention may be formed conventionally. The salts may be formed for example by reaction of the base compound of formula (I) with a pharmaceutically acceptable organic or inorganic acid.

N-oxides of the nitrogen atom of the bicyclic ring system are produced by reaction of a compound of formula (I) with an organic peracid, such as m-chloroperbenzoic acid in, for example, a chlorinated hydrocarbon solvent at below ambient temperature.

Quaternary ammonium salts may be prepared by reaction of a compound of the present invention with the appropriate alkyl, aryl or aralkyl chloride, bromide or iodide. This reaction may be carried out in a solvent, such as acetone, methanol, ethanol, dimethylformamide, at ambient or elevated temperature with or without pressure.

It will be apparent that compounds of the formula (I) containing an $R_1$, $R_2$, $R_3$ or $R_{16}$ group which is convertible to another $R_1$, $R_2$, $R_3$ or $R_{16}$ group are useful novel intermediates. A number of such conversions is possible not only for the end compounds of formula (I), but also for their intermediates as follows:

(a) a hydrogen substituent is convertible to a nitro substituent by nitration;
(b) a nitro substituent is convertible to an amino substituent by reduction;
(c) a $C_{1-7}$ carboxylic acylamino substituent is convertible to an amino substituent by deacylation;
(d) an amino substituent is convertible to a carboxylic $C_{1-4}$ acylamino substituent by acylation; with a carboxylic acid derivative;
(a) a hydrogen substituent is convertible to a halogen substituent by halogenation;
(f) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;
(g) an amino, aminocarbonyl, aminosulphonyl, aminosulphonylamino or N-(aminosulphonyl)-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkyoxy and nitro, or substituted by $C_{4-5}$ polymethylene, by N-alkylation;
(h) an amino substituent is convertible to a $C_{1-6}$ alkylsulphonylamino group or an aminosulphonylamino group, optionally N-substituted as defined, by acylation with a $C_{1-6}$ alkylsulphonic acid or optionally N-substituted carbamic acid derivative.
(i) a $C_{1-4}$ alkylamino substituent group is convertible to an N-($C_{1-6}$ alkylsulphonyl) $C_{1-4}$ alkylamino group or an N-(amino sulphonyl)-$C_{1-4}$ alkylamino group optionally N-substituted as defined by acylation with a $C_{1-6}$ alkylsulphonic acid or optionally N-substituted carbamic acid derivative.

Conversions (a) to (i) are only exemplary and are not exhaustive of the possibilities.

In regard to (a), nitration is carried out in accordance with known procedures.

In regard to (b), the reduction is carried out with a reagent suitable for reducing nitroanisole to aminoanisole.

In regard to (c), deacylation is carried out by treatment with a base, such as a alkyl metal hydroxide.

In regard to (d), (h) and (i) the acylation is carried out with an acylating agent, such as the corresponding acid or acid chloride. Formylation is carried out with the free acid.

In regard to (e), halogenation is carried out with conventional halogenating agents.

In regards to (f), oxidation is carried out below ambient temperatures in a non-aqueous solvent, such as a chlorinated hydrocarbon, in the presence of an organic paracid, such as 3-chloroperbenzoic acid, or in water in the presence of a soluble stong inorganic oxidant, such as an alkali metal permanganate or in aqueous hydrogen peroxide. It will be realised that this process may also N-oxidise the side-chain amine moiety and suitable precautions will routinely be taken by the skilled man.

In regard to (g), alkylation is carried out with a corresponding alkylating agent such as the chloride or bromide under conventional conditions.

Before carrying out any of these conversions, the effect, if any, on other substituents should be considered, and such reagents as are appropriate should be selected together with the adoption of such precautionary measures as are necessary. For example O-alkylation and O-acylation may also produce N-alkylated and N-acylated products respectively unless the nitrogen atom(s) is (are) previously protected. This may be conviently achieved by carrying out the alkylation or acylation reaction in a strong acid, such as trifluoro acetic acid, which protonates, and thereby protects, the nitrogen atom(s).

Compounds of the formula (XXIII) are novel intermediates and thus form an aspect of the present invention.

Compounds of formula (XXII) are either known compounds or are preparable analogously to or routinely derivable from known compounds.

By way of example compounds of the formula (XXII) wherein $Q_6$ and $Q_7$ are not together oxo may be prepared from a corresponding compound of formula (XXIV):

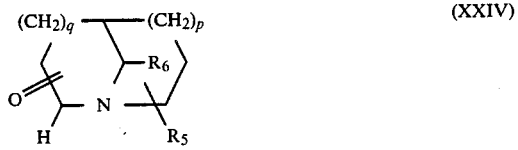

(XXIV)

that is of formula (XXII) wherein $Q_6$ and $Q_7$ together are oxo (i) by conversion thereof to the oxime and reduction of the oxime with a metal hydride in a similar manner to that described in West Germany Offenlegungsschrift No. 28 48 260.6, to give the compound of formula (XXII) wherein $Q_6$ is $NH_2$ and $Q_7$ is H;

(ii) by reacting it with tosyslmethylisonitrile, hydrolysing the resultant nitrile to the corresponding acid and converting the acid OH function to $Q_8$ all conventionally, to give the compound of formula (XXII) wherein $Q_6$ is $COQ_8$ where $Q_8$ is a group readily displaceable by a nucleophile and $Q_7$ is hydrogen;

15

(iii) by conventional oxo to thiooxo conversion to give the compound of formula (XXII) wherein $Q_6$ and $Q_7$ together are thiooxo, or by reduction to the corresponding alcohol and conventional conversion of the alcohol hydroxy group to a readily displaceable group $Q_6$ to give the compound of formula (XXII) wherein $Q_6$ is a group readily displaceably by a nucleophile and $Q_7$ is H.

The intermediates of formula (XXIV) are either known compounds or can be prepared by analogus processes to known compounds.

Compounds of the formula (XXIII) wherein $j^1$ is 2 are conveniently prepared from intermediates of the formula (XXII) by conversion to the nitrile of formula (XXV)

(i)

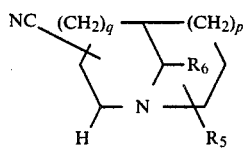

(XXV)

using p-toluene-methyl isocyanide by a procedure analogous to that described by Oldenziel, Van Leusen and van Leusen (J. Org. Chem. 1977, 42, 3114), followed by reduction of the nitrile of formula (XXV) to the corresponding desired amine of formula (XXIII) either with a metal hydride or catalytically. An example of a metal hydride is lithium aluminium hydride in a solvent such as ether or tetrahydrofuran.

Alternatively the nitrile may be hydrolysed to the corresponding acid of formula (XXII), the acid converted to its amide, and the amide reduced to the desired amine of formula (XXIII) wherein $j^1$ is 2. These reactions are effected conventionally.

Again, reaction of a compound of formula (XXII) wherein $Q_6$ is a group readily displaceable by a nucleophile and $Q_7$ is H with sodium cyanide in a suitable solvent such as DMSO will give the nitrile of formula (XXV) above, which may be reduced to the desired amine.

(ii) by Reformatsky reaction with ethyl bromoacetate and zinc to give the ester of formula (XXVI):

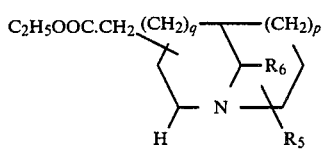

(XXVI)

which may then be hydrolysed to the desired acid of formula (XXIII) wherein $j^1$ is 2 and $Q_6$ is $COQ_8$ as defined and then optionally converting the acid conventionally to its halide, anyhydride or active ester.

(iii) by reduction of the acid of halide of formula (XXII) wherein $Q_6$ is $COQ_8$ and $Q_7$ is H, to give the aldehyde of formula (XXIII) wherein $j^1$ is 2 and $Q_6$ and $Q_7$ together are oxo; or by reducing the acid of formula (XXII) wherein $Q_6$ is COOH to the alcohol of formula (XXVII):

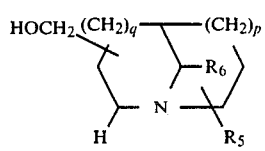

(XXVII)

by a metal hydride such as lithium aluminium hydride; and this alcohol in turn converted the compound of formula (XXVIII):

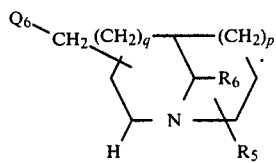

(XXVIII)

with a suitable reagent such as thionyl, mesyl or tosyl chloride.

The foregoing processes described for the interconversion of compounds of formulae (XXII) and (XXIII) where $j^1$ is 1 or 2, are also applicable for the interconversion of compounds of formula (XXIII) where $j^1$ is 1,2,3 or 4.

Compounds of the formula (XXII) and (XXIII) wherein the moiety $Q_6Q_7$ or $Q_6Q_7CH(CH_2)_{j1-1}$—meets the ring at the carbon atom adjacent the ring nitrogen atom may also be prepared by generally analogous procedures, but will of course be appreciated that only such compounds which (will) fulfil the N—N separation proviso of formula (I) are within the scope of this invention.

Compounds of the formula (XXII) or (XXIII) wherein $R_{16}$ is alkyl may be prepared from the corresponding $R_{16}$ is hydrogen compounds by acylation followed by reduction. The acylation will be carried out using formic acid followed by reduction to give the $R_{16}$ is methyl compound. The reduction is suitably carried out using lithium aluminium hydride.

Compounds of the formula (XVIII) are either known compounds or, if novel, are preparable analogously to or routinely derivable from known compounds.

For example novel compounds of formula (XVIII) wherein T is of formula (XXI) and M-E-J-Z is —CO—NR$_{15}^a$—CO—NR$_{15}^b$ may be prepared by the cyclisation of a compound of formula (XXIX):

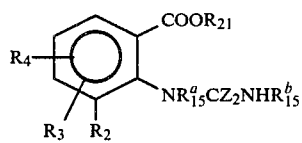

(XXIX)

wherein $R_{15}^a$ and $R_{15}^b$ are each independently $R_{15}$ as defined in formula (III);

$R_{21}$ is hydrogen or $C_{1-6}$ alkyl; and

B, $R_2$, $R_3$ and $R_4$ are as defined in formula (III).

When $R_{21}$ and $R_{15}^b$ are hydrogen in the compound of formula (XXIX) then the cyclisation may suitably be carried out in aqueous conditions at acid pH, for example 25% aqueous acid. Some compounds of the formula (XXIX) can be prepared, conveniently in situ, by reacting a salt $M^+$$^-CNZ_2$, wherein $M^+$ is an alkali metal ion and $Z_2$ is O or S as defined; with a compound of formula (XXX):

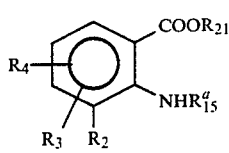

(XXX)

Generation in situ may suitably be achieved using a hydrochloride salt of the compound of the formula (XXX) and reacting that salt with $M^+ {-}CNZ_2$ in aqueous solution at reflux when $Z_2$ is oxygen, or with $M+ -CNZ_2$ in aqueous dichloromethane with a phase transfer catalyst when $Z_2$ is sulphur. When $R_{15}{}^b$ is not hydrogen reaction is with $R_{15}{}^b NCZ_2$ in an inert solvent such as benzene, optionally in the presence of a strong base, particularly if $R_{15}{}^b$ is a sterically hindering group. Sodium ethoxide in benzene, or potassium t-butoxide in toluene, benzene or hexamethyl phosphoramide are suitable reagents.

The compounds of the present invention are dopamine antagonists and may generally be used in the treatment of disorders relating to impaired gastro-intestinal motility, such as retarded gastric emptying, dyspepsia, flatulence, oesphageal reflux and peptic ulcer. Depending on their balance between peripheral and central action on the nervous system, they may also be used in the treatment of emesis and/or the treatment of disorders of the central nervous system, such as psychosis.

The invention therefore also provides a pharmaceutical composition comprising the compound of formula (I), or a pharmaceutically acceptable salt or N-oxide thereof, or a solvate of any of the foregoing and a pharmaceutically acceptable carrier.

The compositions may be formulated for administration by any route. Clearly the formulation will depend on the specific nature of the general activity shown by the chosen compound of the formula (I), and on other factors such as preference in a particular area of therapy for a particuar mode of administration of the compositions, although in general oral administration is preferred. The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice.

A particular composition of the invention is a tablet containing the required amount of a compound of the invention in the form of a powder or granulate compressed in intimate mixture with a lubricant, such as magnesium stearate, a filler, such as microcrystalline cellulose, and a disintegrant, such as sodium starch glycolate.

Oral liquid preparations may be in the form for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicle (which may include edible oils), fo example almond oil, fractioneated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a sufactant or wetting agent is included in the composition to facilitate uniform distribution of the compound.

When appropriate the composition of this invention may be presented as an aerosol for oral administration, as a microfine powder for insufflation or as a suppository for rectal or vaginal administration. Suitable unit dose forms include tablets, capsules and powders in sachets or vials, and preferred forms include shaped oral unit doses, such as tablets and capsules.

The compositions may contain from 0.1% to 99% by weight, preferably from 10-60% by weight, of the active material, depending on the method of administration.

The invention further provides a method of treatment of emesis, disorders relating to impaired gastro-intestinal motility or of disorders of the central nervous system in mammals, such as humans, which comprises the administration of an effective amount of a compound of the present invention, or a pharmaceutically acceptable salt thereof, of N-oxide thereof, or a solvent adduct of any of the foregoing as hereinbefore defined, to the sufferer.

An amount effective to treat the disorders hereinbefore described depends on the relative efficacies of the compounds of the invention, the nature and severity of the disorder being treated and the weight of the mammal. However, a unit dose will normally contain 0.1 to 20 mg for example 0.5 to 10 mg, of the compound of the invention. Unit doses will normally be administered more than once a day, for example 2, 3, 4, 5 or 6 times a day such that the total daily dose is normally in the range 0.01 to 10 mg/kg per day.

As is common practice, the compositions will usually be accompanied by written or printed directions for use in the medical treatment concerned.

The invention also provides a compound of the present invention, in particular a compound of formula (I) for use in the treatment of emesis, disorders relating to impaired gastro-intestinal motility or of disorders of the central nervous system.

The compounds of the present invention have the ability to potentiate the effect of conventional analgesics in migrane treatment when administered concomitantly with the analgesic. Accordingly, the present invention also provides a pharmaceutical composition comprising a compound of the present invention and an analgesic. The effective amount of each component of the composition will depend in the usual way on a number of factors such as the nature and severity of the malady to be treated, the weight of the sufferer, and the actual compound used. However, the compound of the present invention and the analgesic, such as aspirin or paracetamol, are present in unit doeses of the composition in amounts generally similar to their usual effective dose.

The composition can be a combination product, for example a tablet or capsule containing both a compound of the invention and an analgesic for oral administration, or a twin pack comprising the two active ingredients made up for separate administration.

The invention accordingly provides a method of treatment of migraine comprising the administration of an effective amount of a compound of the invention and an analgesic.

The present invention further provides a compound of formula (I) for use with an analgesic in the treatment of migraine.

The following Descriptions and Examples illustrate the preparation of compounds of the Invention and the following biological data illustrate their pharmacological, in particular anti-inflammatory activity. In particular the following Examples illustrate the preparation of the compounds of formula (I) and the following Descriptions illustrate the preparation of the intermediates thereto.

DESCRIPTION 1

A compound of formula (D1):

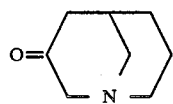

is reacted with hydroxylamine to give the corresponding oxime which is then reduced with sodium in amyl alcohol to give the primary amine.

DESCRIPTION 2

A compound of formula (D2):

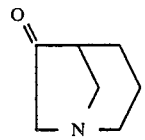

is reacted with hydroxylamine to give the corresponding oxime which is then reduced with sodium in amyl alcohol to give the primary amine.

DESCRIPTION 3

($\pm$) 3-Cycano-1-azabicyclo-[3,3,1]-nonane

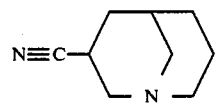

The ($\pm$) 1-azabicyclo-[3,3,1]-nona-3-one was converted into the nitrile by the method of Oldenziel, Van Leusen and Van Leusen (J.O.C. 42 (19), 3114 [1977]). To a stirred solution of the ketone (2.5 g) and (p-toluenesulphonyl)-methyl isocyanide (4.5 g) in ethanol (1.8 ml) and dry dimethoxyethane (80 ml) at 0° C., potassium t-butoxide was added, portionwise, and the resulting suspension stirred at room temperature for 6 hours.

Addition of water (20 ml), saturation of the aqueous layer with potassium carbonate, extraction with ethyl acetate (3×50 ml) and removal of the dried ($K_2CO_3$) extracts afforded the crude nitrile (1.8 g, 70%), i.r. $\nu(C\equiv N)$ 2230 cm$^{-1}$ used without further purification.

DESCRIPTION 4

($\pm$) 3-Aminomethyl-1-azabicyclo-[3,3,1]-nonane

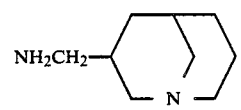

The crude nitrile (1.8 g) in dry THF (20 ml) was added dropwise to a stirred suspension of lithium aluminium hydride (0.5 g) in THF (50 ml) at a sufficient rate as to maintain gentle reflux. After stirring overnight, water (0.5 ml), 15% aqueous sodium hydroxide (0.5 ml) and water (1.5 ml) were added and the solid separated and washed with ethyl acetate (2×50 ml). Removal of the solvent from the filtrate and washings afforded the crude ($\pm$) 3-aminoethyl-1-aza-bicyclo[3,3,1]-nonane as a colourless oil (1.7 g, 90%).

DESCRIPTION 5

($\pm$) 3-Cyano-1-Azabicyclo-[3,2,1]-Octane

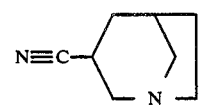

Following the procedures outlines in Description 1, the 1-aza-bicyclo-[3,2,1]-octan-3-one (3.5 g) was converted into ($\pm$) 3-cyano-1-azabicyclo-[3,2,1]-octane (2.5 g, 65%), i.r. $\nu(C{\equiv}N)$ 2230 cm$^{-1}$, used without further purification.

DESCRIPTION 6

(±) 3-Aminomethyl-1-Azabicyclo-[3,2,1]-Octane

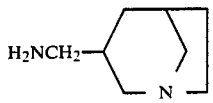
(D4)

Following the procedures outlined in Description 2, the (±) 3-cyano-1-azabicyclo-[3,2,1]-octane (2.5 g) was converted into the crude (±) 3-aminomethyl-1-azabicyclo-[3,2,1]-octane (2.0 g, 80%), used without further purification.

DESCRIPTION 7

(±)4-Amino-1-azabicyclo-[3,3,1]-nonane (D5)

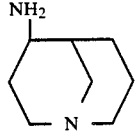
(D5)

To a stirred suspension of lithium aluminium hydride (2.0 g) in dry diethyl ether (100 ml) was added a solution of (±) 1-azabicyclo-[3,3,1]-nonan-4-one oxime (5.0 g) in T.H.F. (50 ml) and the reaction mixture was stirred at ambient temperature for 2 days. Addition of water (2 ml), 2.5N sodium hydride (3 ml) and water (3 ml) followed by filtration gave, on concentration of the filtrate, the crude (±) 4-amino-1-azabicyclo-[3,3,1]-nonane (D5) (3.5 g, 80%).

DESCRIPTION 8

(±) 3-chloromethyl-1-(2'-cyanoethyl)homopiperidine (D6)

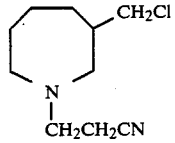
(D6)

A solution of 3-homopiperidyl methanol (9.3 g) in acrylonitrile (5 ml) was stirred at ambient temperatures overnight. The excess acrylonitrile was removed by rotary evaporation and the residue was dissolved in chloroform (100 ml) and treated with thionyl chloride (7 ml). The mixture was heated at reflux for 2 hrs. The cooled reaction mixture was treated with an excess of aqueous sodium bicarbonate solution and the chloroform layer was separated and dried (Na$_2$SO$_4$). Concentration and distillation afforded the (±) 3-chloromethyl-1-(2'-cyanoethyl)homopiperidine (D6) (9.7 g, 67%).

DESCRIPTION 9

(±) 8-cyano-1-azabicyclo-[4,3,1]-decane (D7)

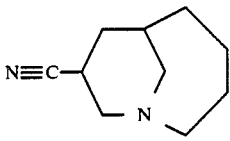
(D7)

To a stirred suspension of sodium hydride (1.5 g, 80%) and potassium t-butoxide (0.5 g) in DMF (100 ml) was added 3-chloromethyl-1-(2'-cyanoethyl)-homopiperidine (D6) (5 g) and the reaction mixture was carefully warmed to 70° C. for 1 hour. On cooling, water (5 ml) was carefully added and the DMF was removed by rotary evaporation. Extraction of the residue with ethyl acetate, concentration and distillation afforded the (±) 8-cyano-1-azabicyclo-[4,3,1]-decane (D7) (4.0 g, 90%) bp 68°–73°/0.1 mm.

DESCRIPTION 10

(±) 8-Aminomethyl-1-azabicyclo-[4,3,1]-decane (D8)

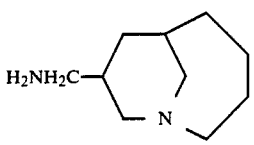
(D8)

Following the procedures outlined in Description 4, the (±) 8-cyano-1-azabicyclo-[4,3,1]-decane (D7) (2.5 g) was converted to (±) 8-aminomethyl-1-azabicyclo-[4,3,1]-decane (D8) (2.2 g, 85%) b.p. 75°–8°/0.1 mm.

EXAMPLE 1

2-Methoxy-4-amino-5-chlorobenzoyl chloride is reacted with the primary amine formed in Description 1 to give the compound of formula (E1):

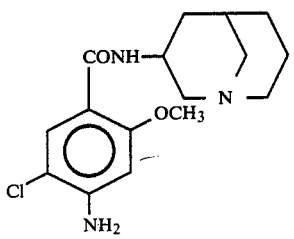
(E1)

EXAMPLE 2

2-Methoxy-4-amino-5-chlorobenzoyl chloride is reacted with the primary amine formed in Description 2 to give the compound of formula (E2):

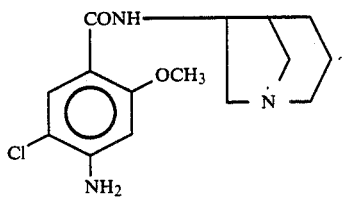
(E2)

EXAMPLE 3

2-Methoxy-5-dimethylaminosulphonylbenzoyl chloride is reacted with the primary amine produced in Description 3 to give a compound of formula (E3):

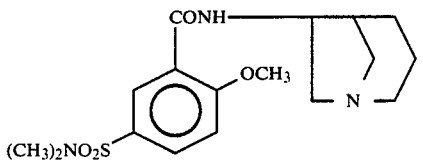
(E3)

EXAMPLE 4

(±)
4-Acetamido-5-chloro-2-methoxy-N-(3'-[1'-azabicyclo-[3,3,1]-nonyl-methyl])benzamide

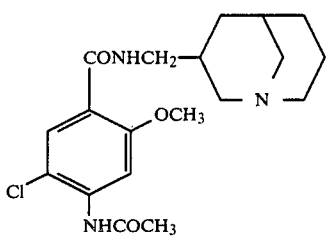
(E4)

4-Acetylamino-5-chloro-2-methoxy-benzoic acid (2.2 g) was heated at 50° with thionyl chloride (20 ml) for 30 minutes. The solvent was evaporated, toluene was added and re-evaporated. The crude acid chloride (3 g) was dissolved in toluene (70 ml), and triethylamine (5 ml) was added, followed by crude (±) 3-aminomethyl-1-azabicyclo-[3,3,1]-nonane (1.7 g). After 30 minutes, dilute sodium hydroxide (10%, 5 ml) was added, and the mixture extracted with ethyl acetate (3×100 ml). The organic extracts were combined, dried and evaporated to give an oily residue. Chromatography on neutral alumina (100 g, 5% deactivated with water) eluting with ethyl acetate afforded (±) 4-acetamido-5-chloro-2-methoxy-N-(3'-[1'-azabicyclo-[3,3,1]-nonylmethyl])benzamide (3 g, 70%, m.p. 165°-8°.

1.72 (1H, s, aromatic H), 1.83 (1H, s, aromatic H), 1.95-2.35 (2H, broad m, CONH and NHCOCH$_3$), 6.02 (3H, s, OCH$_3$), 6.60-9.0 (19H, m, remaining H including 3H singlet at 7.73 for NHCOCH$_3$).

EXAMPLE 5

(±)
4-Amino-5-chloro-2methoxy-N-(3'-[1'-azabicyclo-[3,3,1]-nonylmethyl])benzamide

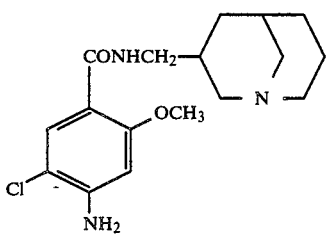
(E5)

The (±) 4-acetamido-5-chloro-2-methoxy-N-(3-[1-azabicyclo-[3,3,1]-nonylmethyl])benzamide (3 g) was heated at reflux with potassium hydroxide (0.5 g) in ethanol (10 ml) and water (2 ml) for 3 hours. Solvent was evaporated and the residue dissolved in ethyl acetate and water.

The ethyl acetate extracts were combined, dried and evaporated to give, after recrystallisation from chloroform/light petroleum, (±) 4-amino-5-chloro-2-methoxy-N-(3'-[1'-azabicyclo-[3,3,1]-nonylmethyl])benzamide (1.7 g, 65%), m.p. 190°-1°.

(d$^6$DMSO): 2,0-2.3 (2H, broad m, CONH including singlet at 2.20 for aromatic 6-H), 3.45 (1H, s, aromatic 3-H), 4.30 (2H, s, NH$_2$), 6.10 (3H, s, OCH$_3$), 6.65-8.80 (16H, m, remaining H).

EXAMPLE 6

(±)
4-Acetamido-5-chloro-2-methoxy-N-(3'-[1'-azabicyclo-[3,2,1]-octyl-methyl])benzamide

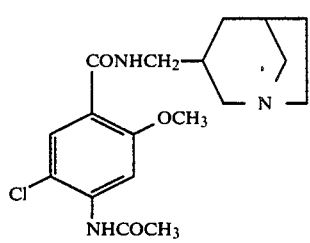
(E6)

Following the procedures outlined in Example 4, the crude (±) 3-aminomethyl-1-azabicyclo-[3,2,1]-octane (2.0 g) was converted into the crude (±) 4-acetamido-5-chloro-2-methoxy-N-(3'-[1'-azabicyclo-[3,2,1]-octyl-methyl])benzamide, isolated as a foam (3.8 g, 60%).

EXAMPLE 7

(±)
4-Amino-5-chloro-2-methoxy-N-(3'-[1'-azabicyclo-[3,2,1]-octyl-methyl])benzamide

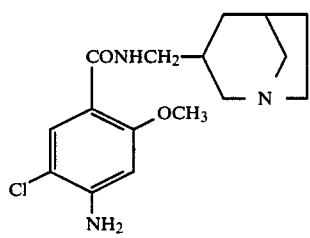
(E7)

Following the procedures outlines in Example 5, the crude (±) 4-acetamido-5-chloro-2-methoxy-N-(3-[1-azabicyclo-[3,2,1]-octyl-methyl])benzamide (3.8 g) was converted to (±) 4-amino-5-chloro-2-methoxy-N-(3'-[1'-azabicyclo-[3,2,1]-octyl-methyl])benzamide, recrystallised from chloroform/ethyl acetate (1.5 g, 45%) mp 185°-6°.

n.m.r. (τ, COCl$_3$): 1.92 (s, 1H, aryl-6-H), 2.1-2.6 (m, 1H, —CONH.CH$_2$—), 3.68 (s, 1H, aryl-3-H), 5.1-5.8 (m, 2H, aryl-NH$_2$), 5.9-8.8 (m, 19H, remaining H including 3H singlet at 6.10 for OCH$_3$).

EXAMPLE 8

(±)
4-Acetamido-5-chloro-2-methoxy-N-(4'-[1'-azabicyclo[3,3,1]-nonyl])benzamide

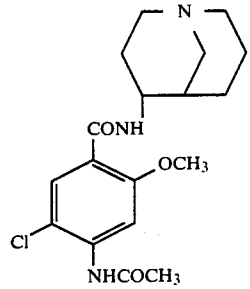

(E8)

Following the procedures outlined in Example 4, the (±) 4-amino-1-azabicyclo-[3,3,1]-nonane (3.5 g) was converted to (±) 4-acetamido-5-chloro-2-methoxy-N-(4'-[1'-azabicyclo-[3,3,1]-nonyl])benzamide (7.2 g, 80%), isolated as an oil.

n.m.r. 1.68 (1H, s, aromatic $\underline{H}$), 1.82 (1H, s, aromatic $\underline{H}$), 1.5-2.3 (2H, broad m, CON$\underline{H}$ and N$\underline{H}$COCH$_3$), 6.0 (3H, s, OC$\underline{H}_3$), 5.5-6.25 (1H, m, CONHC$\underline{H}$=), 6.5-8.6 (16H, m, remaining $\underline{H}$ including 3H singlet at 7.74 for COC$\underline{H}_3$).

EXAMPLE 9

(±)
4-Amino-5-chloro-2-methoxy-N-(4'[1'-azabicyclo-[3,3,1]-nonyl])-benzamide

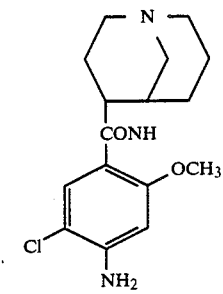

(E9)

Following the procedures outlines in Example 5, the (±) 4-acetamido-5-chloro-2-methoxy-N-(4'-[1'-azabicyclo-[3,3,1]-nonyl])benzamide (7.2 g) was converted to (±) 4-amino-5-chloro-2-methoxy-N-(4-'-[1'-azabicylo-[3,3,1]-nonyl])benzamide (1.2 g, 20%). m.p.>260° (dec).

n.m.r. (d$^6$DMSO) 2.0-2.4 (2H, broad m, CON$\underline{H}$ including singlet at 2.30 for aromatic 6$\underline{H}$), 3.48 (1H, s, aromatic 3$\underline{H}$), 4.1 (2H, broad s, N$\underline{H}_2$), 5.5-6.3 (4H, m, NHC$\underline{H}$= including 3$\underline{H}$ singlet at 6.14 for OC$\underline{H}_3$), 6.8-8.6 (13H, m, remaining $\underline{H}$).

EXAMPLE 10

(±)
4-Acetamido-5-chloro-2-methoxy-N-(8'-[1'-azabicyclo-[4,3,1]-decylmethyl])benzamide

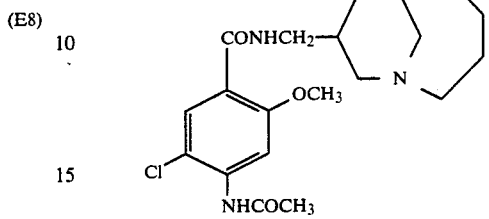

(E10)

Following the procedures outlined in Example 4, the (±) 8-aminomethyl-1-azabicyclo[4,3,1]-decane (D 8) (2.2 g) was converted to the (±) 4-acetamido-5-chloro-2-methoxy-N-(8'-[1'-azabicyclo-[4,3,1]-decylmethyl])benzamide (5.0 g, 89%).

n.m.r. ($\tau$, CDCl$_3$) 1.7-2.5 (m, 4H, CONHCH$_2$, CH$_3$CONH— including 1.97, s, 1H and 2.05, s, 1$\overline{H}$, both aromatic $\overline{H}$), 6.10 (s, 3H, OC$\underline{H}_3$), 6.6-9.0 (m, 21H, remaining $\underline{H}$ including 3H singlet at 7.75 for COC$\underline{H}_3$).

EXAMPLE 11

(±)
4-Amino-5-chloro-2-methoxy-N-(8'-[1'-azabicyclo-[4,3,1]-decylmethyl])benzamide

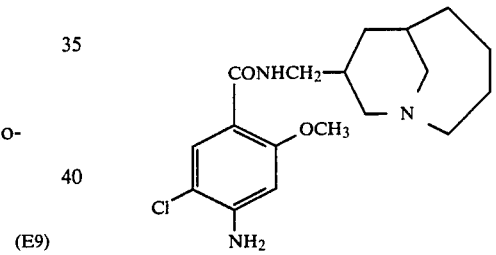

(E11)

Following the procedures outlined in Example 5, the (±) 4-acetamido-5-chloro-2-methoxy-N-(8'-[1'-azabicyclo [4,3,1]-decylmethyl])benzammide (E10) (5.0 g) was converted to (±) 4-amino-5-chloro-2-methoxy-N-(8'-[1'-azabicyclo-[4,3,1]-decylmethyl])benzamide (2.1 g, 48%). m.p. 169°-70°.

n.m.r. ($\tau$, CDCl$_3$) 2.00 (1H, s, aromatic 6$\underline{H}$), 2.00-2.6 (1H, m, CON$\underline{H}$), 3.72 (1H, s, aromatic 3$\underline{H}$), 5.2-5.5-(2H, broad s, N$\underline{H}_2$), 6.16 (3H, s, OC$\underline{H}_3$), 6.6-9.0 (18H, m, remaining $\underline{H}$).

PHARMACOLOGICAL DATA

Gastric Motility

The compound (E5) and (E7) were tested for pharmacological activity in increasing intra-gastric pressure in the rat. Intragastric pressure changes were recorded form previously starved conscious and restrained rats using a saline filled catheter insterted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after the administration of the Compound. Student 't' test was applied to the difference in average values obtained for spontaneous and post compound activity.

At doses of 0.5–1 mg/kg subcutaneously the Compound (E5) and (E7) and significantly increased intragastric pressure. Compound (E9) did so at 0.1 mg/kg.

Inhibition of Apomorphine-induced Biting in the Rat

Apomorphine 5 mg/kg s.c induces a sterotypic gnawing behaviour in rats which can be measured by a subjective scoring system; score 0—animals behave normally; score 1—increased locomotion activity with occasional sniffing and licking; score 2—persistent licking of the bars of the cage with occasional biting; score 3—more sustained biting; score 4—intense biting of a particular part of the cage, animal no longer moving about.

Animals are individually placed in wire cages and after being allowed to become aclimatised are injected with apomorphine 5 mg/kg s.c. Sterotypy is scored at 10 minute invervals for 90 minutes after apomorphine. Compounds are administered subcutaneously 15 minutes after apomorphine.

Compounds (E5), (E7) and (E9) were inactive at dose 50 mg/kg s.c.

Inhibition of apomorphine induced climbing in the mouse.

Compount (E9) was tested for inhibition of apomorphine induced climbing behaviour in the mouse. This is indicative of dopamine receptor blockade in the central nervous system.

The test is based on that described by Protais, P., Constantin, J. and Schwartz J. C. (1976), Psychopharmacology, 50, 1–6.

Apomorphine 1 mg/kg s.c. induces mice to climb the wall of wire cage (inverted food hopper—11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position they spend the majority of time in, score 0—four paws on floor of cage; score 1—fore paws only on wall; score 2—all paws on wall of cage. The scores at all 3 times and for each mouse are summed and scores for mice drug treated orally 30 min. prior to apomorphine compared to mice receiving apomorphine only. A saline only treated group is also included and any score, generally 5% of maximum taken into account.

Compound (E9) was inactive at 25 mg/kg s.c.

Toxicity

No toxic effects were observed in the above tests.

I claim:

1. A compound of formula (XXII):

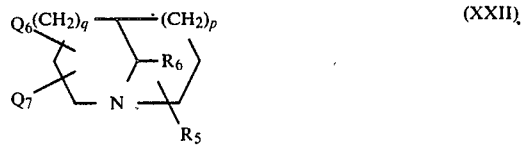

or a compound of formula (XXIII):

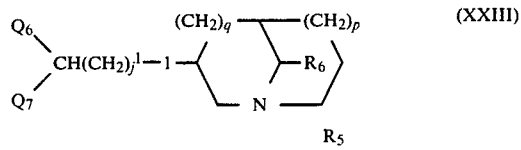

wherein
in formula (XXIII), $j^1-1$ is 1 to 4; and
$Q_6$ and $Q_7$ are on the same carbon atom; and
wherein,
in formulae (XXII) and (XXIII),
$Q_6$ is $NH_2$ and $Q_7$ is H and either p is 0 to 2 and q is 1;
or p is 1 and q is 0 to 3; and
one of $R_5$ and $R_6$ is hydrogen, $C_{1-6}$ alkyl, phenyl or phenyl —$C_{1-3}$ alkyl, which phenyl moieties may be substituted by $C_{1-6}$ alkyl, $C_{1-6}$ alkoxy, $CF_3$ or halogen;
and the other of $R_5$ and $R_6$ is hydrogen or $C_{1-6}$ alkyl.

2. A compound according to claim 1, wherein p is 1.
3. A compound according to claim 2, wherein q is 0, 1, or 2.
4. A compound according to claim 3, wherein q is 1.
5. A compound according to claim 1, wherein $R_6$ is hydrogen or $C_{1-6}$ alkyl.
6. A compound according to claim 1, wherein $Q_6$ or $Q_6Q_7(CH)(CH_2)j$ is beta to the ring nitrogen.
7. A compound of formula XXIII according to claim 1, wherein $j^1-1$ is selected from 1 or 2.
8. A compound of XXIII according to claim 7, wherein $j^1-1$ is 1.
9. A compound selected from the group consisting of (±)3-Aminomethyl-1-azabicyclo-[3,3,1]-nonane, (±)3-Aminomethyl-1-azabicyclo-[3,2,1]-octane, (±)4-Amino-1-azabicyclo-[3,3,1]-nonane and (3S)8-Amino-1-azabicyclo-[4,3,1]-decane.
10. (±)4-Amino-1-azabicyclo-[3,3,1]-nonane, according to claim 9.
11. The compound (±)-Amino-1-azabicyclo-[3,2,1]-octane.

* * * * *